US008167830B2

(12) United States Patent
Noriega

(10) Patent No.: US 8,167,830 B2
(45) Date of Patent: May 1, 2012

(54) METHODS AND SYSTEMS FOR LOW FREQUENCY MECHANICAL TREATMENT OF THE PROSTATE

(76) Inventor: Gerardo V. Noriega, Mountain View, CA (US)

( * ) Notice: Subject to any disclaimer, the term of this patent is extended or adjusted under 35 U.S.C. 154(b) by 97 days.

(21) Appl. No.: 11/963,447

(22) Filed: Dec. 21, 2007

(65) Prior Publication Data

US 2008/0154160 A1 Jun. 26, 2008

Related U.S. Application Data

(60) Provisional application No. 60/871,897, filed on Dec. 26, 2006.

(51) Int. Cl.
*A61B 17/20* (2006.01)

(52) U.S. Cl. .......... 604/22

(58) Field of Classification Search .......... 604/22, 604/544

See application file for complete search history.

(56) References Cited

U.S. PATENT DOCUMENTS

| | | | | |
|---|---|---|---|---|
| 4,813,429 | A | 3/1989 | Eshel et al. | |
| 4,967,765 | A | 11/1990 | Turner et al. | |
| 5,243,997 | A | 9/1993 | Uflacker et al. | |
| 5,330,518 | A | 7/1994 | Neilson et al. | |
| 5,380,273 | A | 1/1995 | Dubrul et al. | |
| 5,419,763 | A | 5/1995 | Hildebrand | |
| 5,454,782 | A | 10/1995 | Perkins | |
| 5,496,271 | A | 3/1996 | Burton et al. | |
| 5,836,951 | A * | 11/1998 | Rosenbluth et al. | 606/108 |
| 6,123,083 | A | 9/2000 | McGrath et al. | |
| 6,322,583 | B1 * | 11/2001 | Tu et al. | 607/96 |
| 6,389,313 | B1 | 5/2002 | Marchitto et al. | |
| 6,433,464 | B2 * | 8/2002 | Jones | 310/328 |
| 6,508,782 | B1 * | 1/2003 | Evans et al. | 604/22 |
| 6,517,534 | B1 | 2/2003 | McGovern et al. | |
| 6,746,465 | B2 | 6/2004 | Diederich et al. | |
| 7,261,710 | B2 | 8/2007 | Elmouelhi et al. | |
| 2002/0003385 | A1 * | 1/2002 | Jones | 310/334 |
| 2003/0073902 | A1 | 4/2003 | Hauschild et al. | |
| 2005/0197627 | A1 | 9/2005 | Huang et al. | |

OTHER PUBLICATIONS

International Search Report and Written Opinion of PCT Application No. PCT/US2007/088653, mailed May 16, 2008, 11 pages.

* cited by examiner

*Primary Examiner* — Christopher D Koharski
*Assistant Examiner* — Diva K Chander
(74) *Attorney, Agent, or Firm* — Venable LLP; Michelle V. Frank

(57) ABSTRACT

Methods and apparatus for treating benign prostatic hyperplasia rely on imparting a low frequency vibration to the prostate. A treatment catheter is introduced through the urethra, and the vibrating element on the catheter energized within the prostate. The low frequency vibration reduces pressure from the prostate on the urethra, possibly by inducing apoptosis of smooth muscle cells.

14 Claims, 5 Drawing Sheets

METHODS AND SYSTEMS FOR LOW FREQUENCY MECHANICAL TREATMENT OF THE PROSTATE

CROSS REFERENCES TO RELATED APPLICATIONS

The present application claims the benefit of prior provisional application No. 60/871,897, filed on Dec. 26, 2006, the full disclosure of which is incorporated herein by reference.

BACKGROUND OF THE INVENTION

1. Field of the Invention

The present invention relates generally to medical devices and methods for their use. More particularly, the present invention relates to methods and devices for treating benign prostatic hyperplasia by applying low frequency vibration to prostatic tissue.

Benign prostatic hyperplasia (BPH), the most common benign neoplasm in males, is a chronic condition that increases in both incidence and prevalence with age. It is associated with progressive lower urinary tract symptoms and affects nearly three out of four men by the seventh decade of life. Benign prostatic hyperplasia is characterized pathologically by a cellular proliferation of the epithelial and stromal elements within the prostate gland P (FIG. 1). As the prostate enlarges, an encapsulating layer of tissue surrounding it inhibits outward expansion, causing the prostate to press against the urethra U like a clamp and also causing a thickening of the bladder wall. The bladder begins to contract even when it contains small amounts of urine, causing more frequent urination. Eventually, the bladder weakens and loses the ability to empty itself, so some urine always remains in the bladder. The narrowing of the urethra and partial emptying of the bladder cause many of the problems associated with BPH.

BPH may be treated with drugs, surgically, or with newly developed minimally invasive techniques. Of particular interest to the present invention, the surgical techniques typically involve resection of tissue in a procedure referred to as transurethral resection of the prostate (TURP). In TURP procedures, a resection blade or tool is introduced through the urethra and employed to resect or core tissue through the urethral wall. While often effective, the procedure is painful, has a relatively long recovery, and frequently has side effects such as incontinence and impotence. More recently, less invasive procedures have been developed. In one, referred to as transurethral microwave thermotherapy (TUMT), a microwave antenna is introduced through the urethra and directs microwave energy to heat the prostate to destroy tissue. The heat, however, presents a substantial risk of injury to the urethral wall, even when measures are taken to provide cooling. A second new procedure, referred to as transurethral needle ablation (TUNA), relies on transurethral introduction of a catheter and advancement of a radiofrequency needle into the prostate. While theoretically exposing the urethral wall to less heat, there is still a risk of injury to the urethra, although fewer side effects are observed. Nonetheless, the recovery time for the injured tissue can still be considerable and the use of the radiofrequency energy presents certain risks to the patient.

For these reasons, it would be desirable to provide improved methods and systems for treating benign prostatic hyperplasia (BPH). Such methods and systems should minimize the risks and side effects associated with BPH treatment and preferably have a shortened recovery time. In particular, the risk of incontinence and impotence should be greatly reduced and preferably eliminated entirely. It would be still further desirable if the methods and systems did not rely on necrosing tissue, thus avoiding the inflammatory and other responses initiated by tissue necrosis. The methods and systems should be reliable, low cost, and effective. At least some of these objectives will be met by the inventions described below.

2. Description of the Background Art

U.S. Pat. No. 5,380,273 describes a low frequency vibrating catheter used to disrupt clot in the vasculature. Patents describing transurethral prostate treatments include U.S. Pat. Nos. 4,813,429; 4,967,765; 5,330,518; 5,419,763; 5,454,782; 5,496,271; 6,123,083; 6,389,313; 6,517,534; 6,746,465; and 7,261,710.

BRIEF SUMMARY OF THE INVENTION

The present invention provides methods and apparatus for treating benign prostatic hyperplasia (BPH) which overcome at least some of the shortcomings of prior treatment modalities as discussed above. In particular, the methods and devices of the present invention can achieve a size reduction in a prostate with minimum trauma and relatively short recovery times. The present invention relies on applying low frequency mechanical vibration to the prostate using a vibrating treatment element positioned within the urethra. The element is vibrated at a frequency in the range from 20 Hz to 200 Hz, preferably from 30 Hz to 100 Hz, and more preferably from 30 Hz to 60 Hz. The vibration is preferably in a lateral direction, but may also include axial, rotational, and more complex vibrational patterns. The extent of lateral displacement imparted against the inner wall of the urethra may vary, typically being in the range from 2 mm to 5 mm, preferably from 1 mm to 2 mm. The vibration is usually achieved by mechanically energizing a treatment element disposed within the urethra, such as rotating an eccentric weight coupled to the treating element, rotating an asymmetric drive shaft coupled to the treating element, or the like. The mechanical motion may be achieved using a motor disposed on a device located in situ within the urethra or alternatively using a drive shaft disposed axially within a device introduced into the urethra. The motor may be electric, hydraulic, fluidic, or have any one of a variety of other configurations. Alternatively, the mechanical vibration could be achieved using a piezoelectric source mechanically configured to reduce the frequency of vibration. Other driving elements include bi-metallic elements driven by an alternating current, spring elements driven by an oscillating tension member, and the like.

While the vibrating elements could be introduced in a variety of ways, they will typically be incorporated on or in a catheter or other device having a shaft configured for insertion into the male urethra from the external opening. The length of the catheter or other advancement shaft will typically be in the range from 10 cm to 60 cm, usually from 20 cm to 40 cm, while the diameter will usually be in the range from 1 mm to 10 mm, usually from 3 mm to 6 mm.

The vibrating elements will usually be mounted at or near a balloon which helps transfer vibrational energy from the vibrating element into tissue surrounding the balloon (when inflated). Most commonly, the vibrating element(s) will be on the shaft within the interior of the balloon. In that case, the energy will be transferred through the balloon inflation medium (e.g., saline) into the prostatic tissue. In other embodiments, the vibrating element will be positioned in or on the shaft with a balloon asymmetrically positioned on the shaft to push a surface of the shaft directly against the urethral wall. In still other configurations, the vibrating element may be positioned on an outer surface of a balloon or other expandable structure so that expansion of the structure will engage the vibrating element directly against the urethral wall.

The treatment devices of the present invention may further comprise an anchoring element for stabilizing and positioning the device within the urethra during the treatment. For example, an inflatable balloon or other expandable anchor may be provided on the shaft which carries the vibrating treatment element. Typically, the anchor will be disposed distally of the treating element so that it may be deployed within the bladder to stabilize and position the vibrating treatment element within the prostate. In addition to balloons, the anchor could comprise a mallecot structure, a deflectable distal end, or other conventional expansible element which may be expanded within the bladder and pulled back against the bladder wall to position the shaft of the device.

Further optionally, the treatment devices may include an injector or other means for delivering a therapeutic substance into the prostate as part of the treatment protocol. Typically, the injector will comprise at least one needle which is laterally advanceable from the device shaft. While, in the illustrated embodiments below, the needle is shown to be disposed distally of the vibrating treatment element, it could also be disposed proximally. The delivery of a therapeutic agent may occur before vibrational treatment, concurrently with vibrational treatment, or subsequent to vibrational treatment. Moreover, it would be possible to move the treating device before or after treatment in order to position or reposition the injector to deliver the substance to different locations. Exemplary therapeutic and analgesic substances which may be delivered include lidocaine, alpha blockers, smooth muscle cell contracting stimulants, and the like.

The catheter or other treatment device may optionally be coated with a hydrophilic, hydrophobic, and/or antibiotic material to facilitate insertion of the device through the urethra and/or minimize injury to the urethra. Other substances which may be used to coat the device include anti-inflammatory drugs.

Although the precise mechanism of action in the treatments of the present application is not known, it is presently believed that the low frequency vibration induces apoptosis or "programmed cell death" within the smooth muscle cells (SMC's) which are present within the prostate and largely responsible for hyperplasia. As apoptosis results in less inflammation and trauma, a volumetric reduction in the prostate may be achieved with fewer side effects than are associated with radiofrequency ablation, surgical or minimally invasive excisions, and the like.

DETAILED DESCRIPTION OF THE INVENTION

Figure 1:
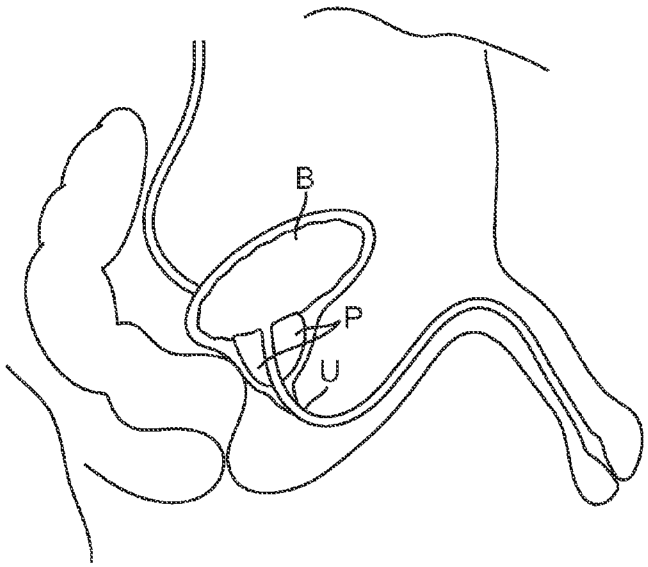
FIG. 1 illustrates the anatomy of the urethra U, prostate P, and bladder B.

As shown in FIG. 1, the prostate P is located near the distal end of the male urethra U adjacent the opening or os into the bladder B. The methods and apparatus of the present invention are intended for introduction through the urethra to place a vibrating element within the prostate P. Optionally, an anchoring element will be positioned within the bladder to stabilize the treatment device while it is being used to apply the desired low frequency vibration. Still further optionally, needles or other injectors may be deployed to deliver drugs and/or analgesics into the prostate as part of the treatment.

Figure 2:
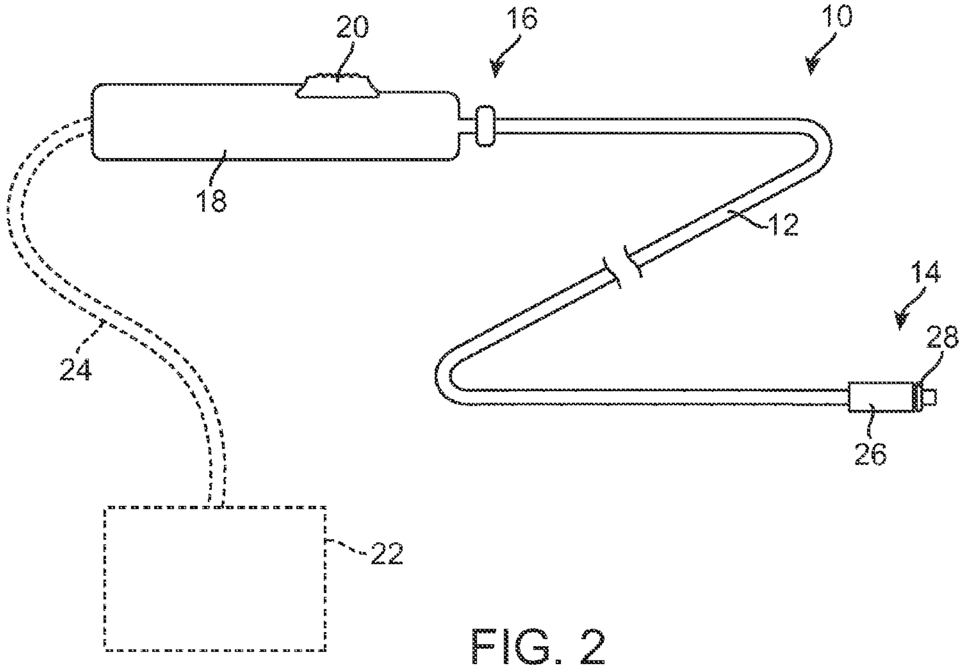
FIG. 2 illustrates an exemplary treatment device constructed in accordance with the principles of the present invention.

Referring now to FIG. 2, a treatment device 10 constructed in accordance with the principles of the present invention includes a shaft 12 having a distal end 14 and a proximal end 16. Shaft 12 will typically comprise a flexible polymeric extrusion having at least one axial lumen, usually having two or more axial lumens. The shaft could be reinforced, for example with braids, axial wires, or the like, but typically will not need to be. Suitable extrudable polymers include polyamides (nylons), polyether block amides (PEBAX), high density polyethylenes, and the like.

The treatment device 10 further includes a handle 18 attached to the proximal end 16 of the shaft 12. The handle will typically include a thumb switch or other trigger 20 which permits the user to turn on and off the vibration. Alternatively, a foot switch (not shown) could be used. Optionally, handle 18 may be connected to an external unit 22 (shown in broken line) by a cable or other cord 24 to provide energy, drug delivery, control functions, or the like.

Figure 3:
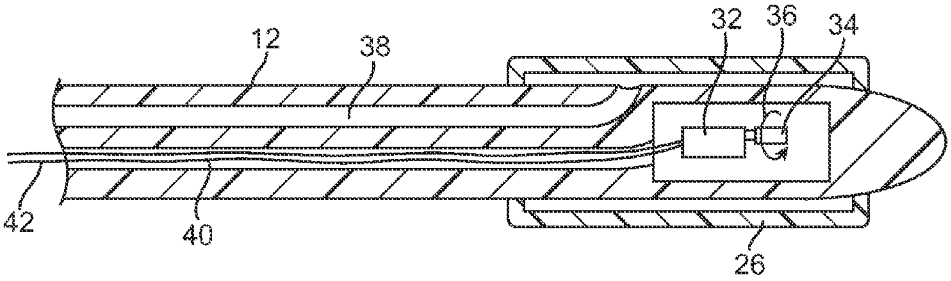
FIG. 3 illustrates a first exemplary vibrational element including a motor and eccentric weight which may be carried within the balloon of the treatment device of FIG. 2.
Figure 4:
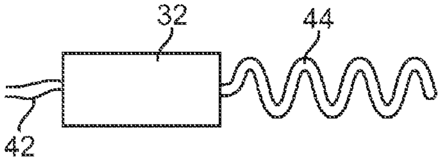
FIG. 4 illustrates a motor and a symmetric drive shaft which may be carried by the treatment device of FIG. 3.

A balloon 26 is positioned near the distal end 14 of the shaft 12, and typically one or more radioopaque markers 28 will be provided adjacent to and/or within the balloon to facilitate fluoroscopic imaging. As shown in FIGS. 3-6, a vibrating element will be disposed within the balloon. In particular, as shown in FIG. 3, a motor 32 may be positioned within the distal end of the shaft and connected to an eccentric weight 34. The motor will rotate the eccentric weight about a central axis, as illustrated by arrow 36, causing lateral vibration of the distal end of the shaft. The exact frequency and displacement of the vibration can be controlled by appropriate choice of the speed of motor and mass of the weight. The shaft 12 of the device shown in FIG. 3 will have at least two lumens. A first lumen 38 is provided for inflating the balloon 26 and a second lumen 40 is provided for routing wires or other conductors 42 needed to power the motor 32. The motor 32 of FIG. 3 could be connected to other elements for imparting the desired vibration, including an asymmetric drive shaft 44, as shown in FIG. 4.

Figure 3A:
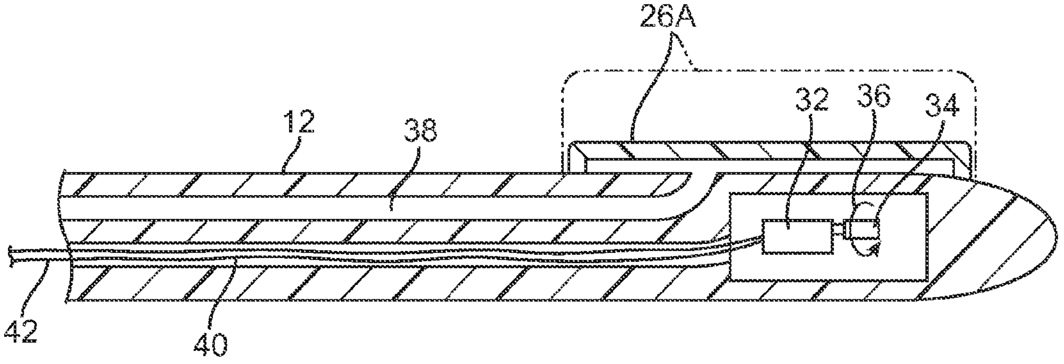
FIG. 3A illustrates a vibrational element similar to that illustrated in FIG. 3 with an asymmetric balloon oriented to engage the element against a urethral wall.

In FIG. 3A, a vibrating element similar to that illustrated in FIG. 3 is shown mounted adjacent to an asymmetrically positioned balloon 26A. The balloon 26A is mounted to inflate on one side of the shaft 12 only, as shown in broken line. In that way, the opposite surface of the shaft may be engaged directly against the urethral wall to selectively direct the vibrational energy.

Figure 6:
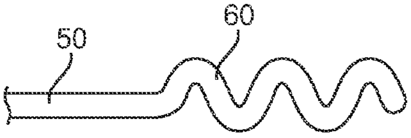
FIG. 6 illustrates an axial drive shaft having an asymmetric distal end which may be carried by the treatment device of FIG. 5.
Figure 5:
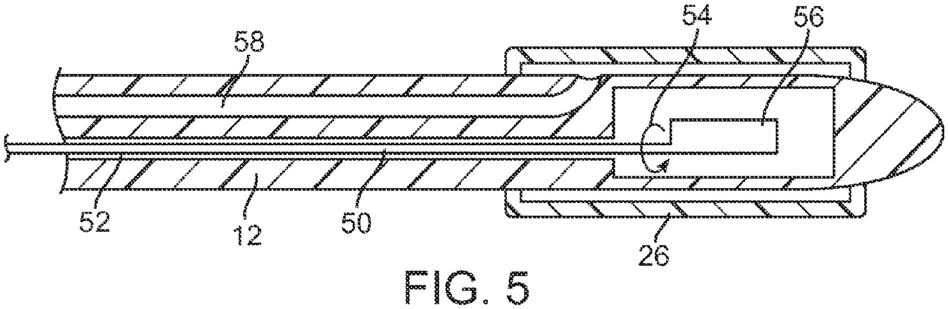
FIG. 5 illustrates a second exemplary vibrational element including an axial drive shaft and an eccentric weight which may be carried by the treatment device of FIG. 2.

An alternative vibrating element structure is illustrated in FIG. 5. In FIG. 5, the shaft 12 has an axial drive shaft 50 which extends from the proximal end of the shaft to the distal end, typically through a drive shaft lumen 52. A motor may be provided within the handle 18 (FIG. 2) in order to rotate the shaft shown by arrow 54 An eccentric weight 56 may be attached to the distal end of the shaft in order to transmit vibrations to the shaft within the balloon 26. A separate balloon inflation lumen 58 will be provided. As an alternative to the eccentric weight 56, the drive shaft 50 may have an asymmetric structure 60 at its distal end, as shown in FIG. 6.

Figure 7:
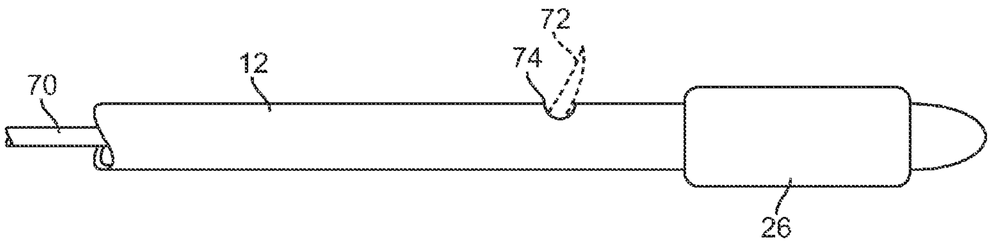
FIG. 7 illustrates a treatment device similar to that shown in FIG. 2, but further including a tissue injector which may be deployed from the device.

The treatment devices of the present invention may be combined with other features to enhance their utility and effectiveness. For example, as shown in FIG. 7, a laterally deployable injector 70 may be provided within a separate lumen within the shaft 12. Typically, a distal end 72 of the needle (shown in broken line) will be adapted to deploy laterally through a port 74 in the shaft so that it may be directed into the prostatic tissue from the urethra. The other elements of the treatment device may remain as described previously.

Figure 8:
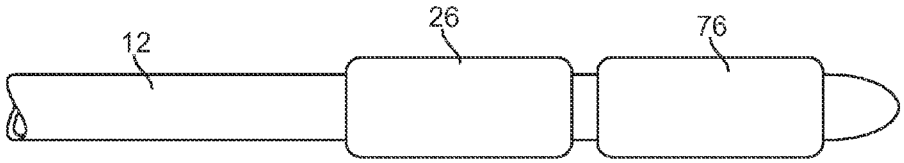
FIG. 8 illustrates a treatment device similar to that shown in FIG. 2, but further including a distal anchor member.
Figure 9:
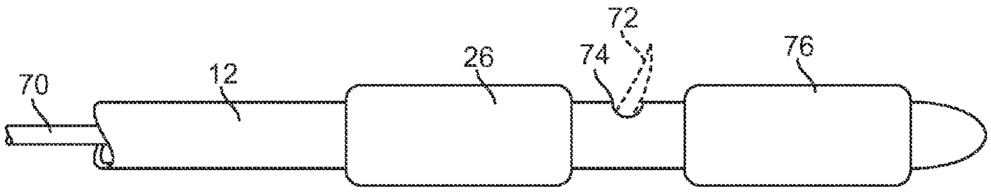
FIG. 9 illustrates a treatment device similar to that shown in FIG. 2, including both an injector and a distal anchor.

As shown in FIG. 8, a stabilizing balloon 76, or other expandable element such as a malecot, may be provided distally of the treatment balloon 26. The anchor 76 will be positioned to be expanded within the bladder to provide both forced stabilization and positioning of the treatment balloon 26 within the prostate. As shown in FIG. 9, both the injector 70 and the stabilizing element 76 may be combined on a single shaft 12.

Figure 10A:
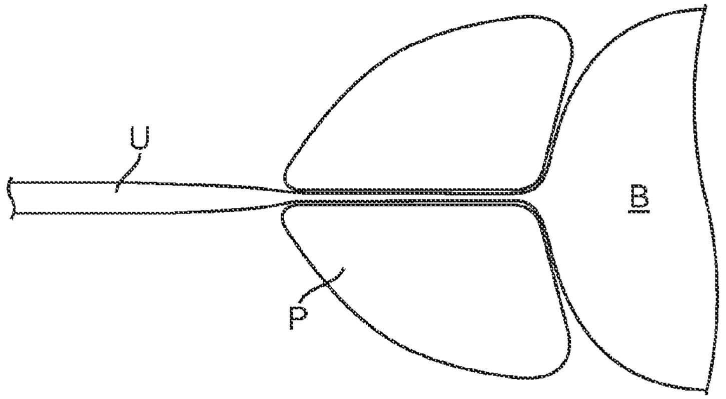
FIGS. 10A-10C illustrate use of the treatment device of FIG. 2 for treating BPH.
Figure 10B:
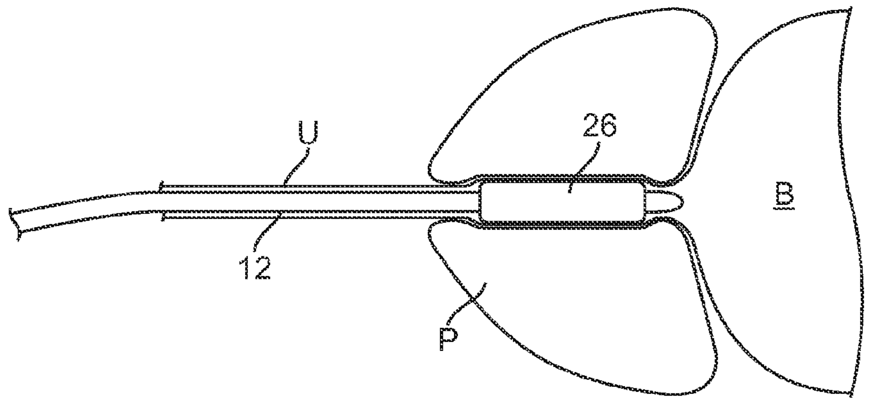
Figure 10C:
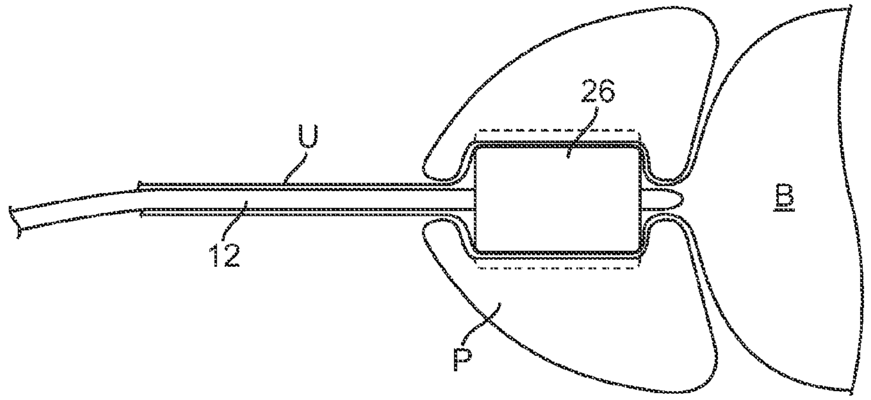

Referring now to FIGS. 10A-10C, use of the device 10 for treating a prostate P will be described. As shown in FIG. 9A, the prostate P surrounds a distal end of the urethra U adjacent the bladder B. The shaft 12 may be advanced through the urethra U so that the treatment balloon 26 is disposed within the prostate P adjacent the bladder B, as shown in FIG. 10B. Optionally, a stabilizing element may be advanced within the bladder and inflated or expanded to permit pullback of the shaft 12 to enhance positioning and stability (not shown). Once proper positioning of the shaft 12 and treatment balloon 26 is confirmed using a cystoscope or fluoroscopically, the treatment balloon 26 may be expanded, as shown in FIG. 10C. The balloon thus engages the inner wall of the urethra and expands against the prostate P. The vibrating element is then energized, causing the balloon to vibrate, usually in a lateral direction as shown by the broken line in FIG. 10C. The treatment will then be performed at the frequencies and displacements described above, typically for a time in the range from 30 minutes to 60 minutes. Treatment may be performed more than once in any session, and may be repeated as often as the hyperplasia recurs.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for successfully treating benign prostate hyperplasia, the method comprising:

delivering vibrational energy to tissue in the prostate sufficient to induce apoptosis in smooth muscles in the prostate sufficient to produce a volumetric reduction in the prostate and successfully treat the hyperplasia, wherein the vibrational energy is delivered from within the prostate from a treatment element disposed within a urethra, wherein a treatment element induces is laterally displaced at a frequency of from 20 Hz to 200 Hz, and wherein the treatment element has a lateral displacement amplitude of 1 mm to 5 mm.

2. A method as in claim 1, further comprising:

introducing the treatment element in a urethra proximate a prostatic constriction; and vibrating the treatment element to relieve prostatic constriction.

3. The method of claim 1, wherein the lateral displacement of the treating element has an amplitude in the range from 1 mm to 2 mm.

4. The method of claim 1, wherein vibrational energy is provided by rotating an eccentric weight coupled to the treatment element.

5. The method of claim 1, wherein vibrational energy is provided by rotating an asymmetric drive shaft.

6. The method of claim 1, wherein the treating element comprises a balloon surrounding a vibrating element, further comprising inflating the balloon to engage an inner wall of the urethra adjacent the prostate.

7. The method of claim 1, further comprising expanding an anchoring element to stabilize the treatment element.

8. The method of claim 7, wherein the anchoring element comprises an inflatable balloon.

9. The method of claim 1, further comprising injecting a prostate before, concurrent with, or after delivering vibrational energy.

10. The method of claim 9, wherein the vibrating element is on a catheter and injecting comprises advancing an injection element into the prostate from the catheter.

11. The method of claim 1, wherein vibrating treatment is carried out for a time from the range from 30 minutes to 60 minutes.

12. The method of claim 1, wherein the vibrating treatment is performed more than once in a minute.

13. The method of claim 1, wherein the lateral displacement of the treating element has an amplitude in the range from 2 mm to 5 mm.

14. The method of claim 1, wherein the vibrating element is on a catheter having a shaft and an external surface of the shaft directly engages a urethral wall to deliver the vibrational energy without an inflation balloon.

* * * * *